United States Patent
Jungkamp et al.

(10) Patent No.: US 7,439,381 B2
(45) Date of Patent: Oct. 21, 2008

(54) HYDROCYANATION METHOD

(75) Inventors: Tim Jungkamp, Kapellen (BE); Dagmar Pascale Kunsmann-Keitel, Limburgerhof (DE); Michael Bartsch, Neustadt (DE); Robert Baumann, Mannheim (DE); Gerd Haderlein, Grünstadt (DE); Hermann Luyken, Ludwigshafen (DE); Jens Scheidel, Hirschberg (DE)

(73) Assignee: BASF SE, Ludwigshafen (DE)

( * ) Notice: Subject to any disclaimer, the term of this patent is extended or adjusted under 35 U.S.C. 154(b) by 166 days.

(21) Appl. No.: 10/586,490

(22) PCT Filed: Jan. 26, 2005

(86) PCT No.: PCT/EP2005/000723

§ 371 (c)(1), (2), (4) Date: Jul. 20, 2006

(87) PCT Pub. No.: WO2005/073168

PCT Pub. Date: Aug. 11, 2005

(65) Prior Publication Data

US 2007/0155977 A1    Jul. 5, 2007

(30) Foreign Application Priority Data

Jan. 29, 2004   (DE) .................. 10 2004 004 684

(51) Int. Cl.
    *C07C 253/00* (2006.01)
(52) U.S. Cl. ...................................... 558/322; 558/338
(58) Field of Classification Search ................ 558/322, 558/338
    See application file for complete search history.

(56) References Cited

U.S. PATENT DOCUMENTS

| | | | |
|---|---|---|---|
| 2,571,099 A | 10/1951 | Arthur, Jr. et al. | |
| 3,778,462 A | 12/1973 | Taylor et al. | |
| 3,846,474 A | 11/1974 | Mok | |
| 3,852,329 A | 12/1974 | Tomlinson | |
| 4,382,038 A * | 5/1983 | McGill ...................... | 558/338 |
| 4,714,773 A * | 12/1987 | Rapoport ................... | 558/338 |
| 6,093,285 A * | 7/2000 | Fernald et al. ............. | 203/14 |

FOREIGN PATENT DOCUMENTS

EP    0 274 401 A1    7/1988

* cited by examiner

*Primary Examiner*—Kamal A. Saeed
*Assistant Examiner*—Samantha Shterengarts
(74) *Attorney, Agent, or Firm*—Connolly Bove Lodge & Hutz LLP

(57) ABSTRACT

A process is described for preparing 3-pentenenitrile by hydrocyanating 1,3-butadiene with hydrogen cyanide over at least one catalyst, wherein the 1,3-butadiene and/or hydrogen cyanide is contacted with at least one microporous solid before the reaction.

17 Claims, No Drawings

HYDROCYANATION METHOD

CROSS REFERENCE TO RELATED APPLICATIONS

This application is a National Phase of PCT/EP2005/000723, filed Jan. 26, 2005, which claims priority to German application 102004004684.0, filed Jan. 29, 2004.

The present invention relates to a process for preparing 3-pentenenitrile by hydrocyanating 1,3-butadiene with hydrogen cyanide over at least one catalyst.

Adiponitrile is an important starting material in nylon production and is obtained by double hydrocyanation of 1,3-butadiene. In a first hydrocyanation, 1,3-butadiene is hydrocyanated to 3-pentenenitrile. In a second, subsequent hydrocyanation, 3-pentenenitrile is reacted with hydrogen cyanide to give adiponitrile. Both hydrocyanations are catalyzed by nickel(0)-phosphorus complexes.

The nickel(0)-phosphorus complexes used in the hydrocyanation of 1,3-butadiene are sensitive toward protic compounds such as water, aliphatic or aromatic alcohols. Since 1,3-butadiene and/or hydrogen cyanide generally contain water and tert-butylpyrocatechol (stabilizer of 1,3-butadiene), the nickel(0)-phosphorus complexes have a restricted lifetime.

U.S. Pat. No. 3,852,329 describes a process for isomerizing 2-methyl-3-butenenitrile over a nickel(0)-phosphorus complex as a catalyst to give 3-pentenenitrile. In this isomerization, 2-methyl-3-butenenitrile and/or the catalyst is contacted with a molecular sieve before the actual isomerization. According to U.S. Pat. No. 3,852,329 it is also possible to carry out the isomerization directly in the presence of a molecular sieve.

U.S. Pat. No. 3,846,474 describes a process for hydrocyanating 3-pentenenitrile over a nickel(0)-phosphorus catalyst. In this process, 3-pentenenitrile is contacted with a molecular sieve before the hydrocyanation. Alternatively, it is possible that the molecular sieve is used during the hydrocyanation or the catalyst solution is treated with a molecular sieve before it is used in the hydrocyanation.

It is thus an object of the present invention to provide a process for preparing 3-pentenenitrile by hydrocyanating 1,3-butadiene with hydrogen cyanide over at least one catalyst, the catalyst used in the process having a high lifetime.

The inventive achievement of this object starts from a process for preparing 3-pentenenitrile by hydrocyanating 1,3-butadiene with hydrogen cyanide over at least one catalyst. In a first embodiment, the process according to the invention comprises contacting 1,3-butadiene and/or hydrogen cyanide with at least one microporous solid before the reaction.

The 1,3-butadiene used in the hydrocyanation may contain water as a result of the preparation process. In addition, 1,3-butadiene is typically stored and transported with stabilizers. The stabilizer used is, for example, tert-butylpyrocatechol (TBP).

It has been found in accordance with the invention that the contacting of 1,3-butadiene with the at least one microporous solid increases the lifetime of the nickel(0)-phosphorus catalyst. Without being bound to a theory, the effect of the increased lifetime of the catalyst is attributed to the removal of water and of the tert-butylpyrocatechol stabilizer.

In the process according to the invention, the 1,3-butadiene and the hydrogen cyanide may be contacted together or separately with the at least one microporous solid. It is preferred that the 1,3-butadiene and/or the hydrogen cyanide are freed of the at least one microporous solid before the actual hydrocyanation with the at least one catalyst.

Preference is given to contacting the 1,3-butadiene and/or the hydrogen cyanide in tubes having beds, and the flow conditions of 1,3-butadiene and/or hydrogen cyanide are selected in such a way that plug flow characteristics, i.e. a flow without great radial flow rate differences over the cross section, are generated, so that the backmixing of the system is virtually ruled out.

In a second embodiment, the present invention relates to a process for preparing 3-pentenenitrile by hydrocyanating 1,3-butadiene with hydrogen cyanide with at least one catalyst, the process according to the invention comprising effecting the hydrocyanation in the presence of the at least one microporous solid.

For the hydrocyanation itself according to the first and second embodiment of the process according to the invention, the same conditions described hereinbelow apply:

The phosphorus ligands of nickel(0) complexes and the free phosphorus ligands are preferably selected from mono- or bidentate phosphines, phosphites, phosphinites and phosphonites.

These phosphorus ligands preferably have the formula I

$$P(X^1R^1)(X^2R^2)(X^3R^3) \qquad (I).$$

In the context of the present invention, compound (I) is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1R^2R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified below.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified below.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the R¹, R² and R³ groups should be o-tolyl groups.

Particularly preferred compounds I which may be used are those of the formula Ia

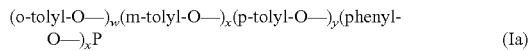

$$(\text{o-tolyl-O—})_w(\text{m-tolyl-O—})_x(\text{p-tolyl-O—})_y(\text{phenyl-O—})_zP \quad (Ia)$$

where w, x, y and z are each a natural number and the following conditions apply: w+x+y+z=3 and w,z≦2, Such compounds Ia are for example (p-tolyl-O—)(phenyl-O—)₂P, (m-tolyl-O—)(phenyl-O—)₂P, (m-tolyl-O—)(phenyl-O—)₂P, (o-tolyl-O—)(phenyl-O—)₂P, (p-tolyl-O—)₂(phenyl-O—)P, (m-tolyl-O—)₂(phenyl-O—)P, (o-tolyl-O—)₂(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)₃P, (m-tolyl-O—)(p-tolyl-O—)₂P, (o-tolyl-O—)(p-tolyl-O—)₂P, (m-tolyl-O—)₂(p-tolyl-O—)P, (o-tolyl-O—)₂(p-tolyl-O—)P, (o-tolyl-O—)(m-tolyl-O—)(p-tolyl-O—)P, (m-tolyl-O—)₃P, (o-tolyl-O—)(m-tolyl-O—)₂P (o-tolyl-O—)₂(m-tolyl-O—)P or mixtures of such compounds.

Mixtures comprising (m-tolyl-O—)₃P, (M-tolyl-O—)₂(p-tolyl-O—)P, (m-tolyl-O—)(p-tolyl-O—)₂P and (p-tolyl-O—)₃P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, suitable phosphorus ligands are the phosphites, described in detail in DE-A 199 53 058, of the formula Ib:

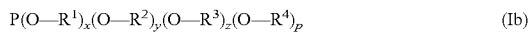

$$P(O—R^1)_x(O—R^2)_y(O—R^3)_z(O—R^4)_p \quad (Ib)$$

where

R¹: aromatic radical having a C₁-C₁₈-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, R²: aromatic radical having a C₁-C₁₈-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, R³: aromatic radical having a C₁-C₁₈-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, R⁴: aromatic radical which bears substituents other than those defined for R¹, R² and R³ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that x+y+z+p=3.

Preferred phosphites of the formula Ib can be taken from DE-A 199 53 058. The R¹ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred R² radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous R³ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The R⁴ radical is preferably phenyl. p is preferably zero. For the indices x, y, z and p in compound Ib, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula Ib are those in which p is zero, and R¹, R² and R³ are each independently selected from o-isopropylphenyl, m-tolyl and p-tolyl, and R⁴ is phenyl.

Particularly preferred phosphites of the formula Ib are those in which R¹ is the o-isopropylphenyl radical, R² is the m-tolyl radical and R³ is the p-tolyl radical with the indices specified in the table above; also those in which R¹ is the o-tolyl radical, R² is the m-tolyl radical and R³ is the p-tolyl radical with the indices specified in the table; additionally those in which R¹ is the 1-naphthyl radical, R² is the m-tolyl radical and R³ is the p-tolyl radical with the indices specified in the table; also those in which R¹ is the o-tolyl radical, R² is the 2-naphthyl radical and R³ is the p-tolyl radical with the indices specified in the table; and finally those in which R¹ is the o-isopropylphenyl radical, R² is the 2-naphthyl radical and R³ is the p-tolyl radical with the indices specified in the table; and also mixtures of these phosphites.

Phosphites of the formula Ib may be obtained by a) reacting a phosphorus trihalide with an alcohol selected from the group consisting of R¹OH, R²OH, R³OH and R⁴OH or mixtures thereof to obtain a dihalophosphorous monoester, b) reacting the dihalophosphorous monoester mentioned with an alcohol selected from the group consisting of R¹OH, R²OH, R³OH and R⁴OH or mixtures thereof to obtain a monohalophosphorous diester and c) reacting the monohalophosphorous diester mentioned with an alcohol selected from the group consisting of R¹OH, R²OH, R³OH and R⁴OH or mixtures thereof to obtain a phosphite of the formula Ib.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites Ib and for the workup can be taken from DE-A 199 53 058.

The phosphites Ib may also be used in the form of a mixture of different phosphites Ib as a ligand. Such a mixture may be obtained, for example, in the preparation of the phosphites Ib.

However, preference is given to the phosphorus ligand being multidentate, in particular bidentate. The ligand used therefore preferably has the formula II

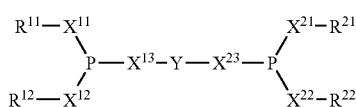

(II)

where
$X^{11}$, $X^{12}$, $X^{13}$, $X^{21}$, $X^{22}$, $X^{23}$ are each independently oxygen or a single bond
$R^{11}$, $R^{12}$ are each independently identical or different, separate or bridged organic radicals
$R^{21}$, $R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite.

In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of 10.30.2003 which has an earlier priority date but had not been published at the priority date of the present application.

The compounds described I, Ia, Ib and II and their preparation are known per se. Phosphorus ligands used may also be mixtures comprising at least two of the compounds I, Ia, Ib and II.

In a particularly preferred embodiment of the process according to the invention, the phosphorus ligand of the nickel(0) complex and/or the free phosphorus ligand is, selected from tritolyl phosphite, bidentate phosphorus chelate ligands and the phosphites of the formula Ib

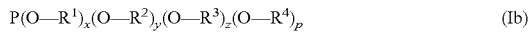
(Ib)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

The hydrocyanation according to the first and second embodiment may be carried out in any suitable apparatus known to those skilled in the art. Useful apparatus for the reaction is customary apparatus, as described, for example, in: Kirk-Othmer, Encyclopedia of Chemical Technology, 4th Ed., Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. It has been found that particularly advantageous batteries of reactors are those having backmixing characteristics and which are operated in crossflow mode in relation to the metering of hydrogen cyanide.

The hydrocyanation may be carried out in batch mode, continuously or in semibatchwise operation.

Preference is given to carrying out the hydrocyanation continuously in one or more stirred process steps. When a plurality of process steps is used, it is preferred that the process steps are connected in series. In this case, the product from one process step is transferred directly into the next process step. The hydrogen cyanide may be added directly into the first process step or between the individual process steps.

When the hydrocyanation is carried out in semibatchwise operation, it is preferred that the reactor is initially charged with the catalyst components and 1,3-butadiene, while hydrogen cyanide is metered into the reaction mixture over the reaction time.

The hydrocyanation may be carried out in the presence or in the absence of a solvent. When a solvent is used, the solvent should be liquid and inert toward the unsaturated compounds and the at least one catalyst at the given reaction temperature and the given reaction pressure. In general, the solvents used are hydrocarbons, for example benzene or xylene, or nitriles, for example acetonitrile or benzonitrile. However, preference is given to using a ligand as the solvent.

The hydrocyanation reaction may be carried out by charging the apparatus with all reactants. However, it is preferred when the apparatus is filled with the at least one catalyst, 1,3-butadiene and, if appropriate, the solvent. The gaseous hydrogen cyanide preferably floats over the surface of the reaction mixture or is preferably passed through the reaction mixture. A further procedure for charging the apparatus is the filling of the apparatus with the at least one catalyst, hydrogen cyanide and, if appropriate, the solvent, and slowly feeding the 1,3-butadiene to the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

The hydrocyanation is carried out preferably at pressures of from 0.1 to 500 MPa, more preferably from 0.5 to 50 MPa, in particular from 1 to 5 MPa. The reaction is carried out preferably at temperatures of from 273 to 473 K, more preferably from 313 to 423 K, in particular at from 333 to 393 K. It has been found that advantageous average mean residence times of the liquid reactor phase are in the range from 0.001 to 100 hours, preferably from 0.05 to 20 hours, more preferably from 0.1 to 5 hours, in each case per reactor.

In one embodiment, the hydrocyanation may be performed in the liquid phase in the presence of a gas phase and, if appropriate, of a solid suspended phase. The starting materials, hydrogen cyanide and 1,3-butadiene, may in each case be metered in in liquid or gaseous form.

In a further embodiment, the hydrocyanation may be carried out in the liquid phase, in which case the pressure in the reactor is such that all reactants such as 1,3-butadiene, hydrogen cyanide and the at least one catalyst are metered in in liquid form and are present in the liquid phase in the reaction mixture. A solid suspended phase may be present in the reaction mixture and may also be metered in together with the at least one catalyst, for example consisting of degradation products of the catalyst system, comprising nickel(II) compounds inter alia.

The microporous solid obtained after the treatment of the 1,3-butadiene and/or hydrogen cyanide, or the microporous solid used in the hydrocyanation, may, after it has been used, be regenerated by heating under reduced pressure in an atmosphere which is formed by gases selected from the group consisting of noble gases, air and oxygen. It is thus possible to use the microporous solid again.

In both embodiments of the process according to the invention, it is preferred that the 1,3-butadiene has a content of acetylene which is less than 1000 ppm, more preferably less than 100 ppm, in particular less than 50 ppm.

The at least one microporous solid used in the process according to the invention is preferably selected from the group consisting of aluminas and molecular sieves, and preferably has a particle size of from 0.01 to 20 mm, more preferably from 0.1 to 10 mm, in particular from 1 to 5 mm. The porosity of the shaped bodies is between 0 and 80% based on the particle volume. It is possible to use particles either in the form of extrudates or in round form, or in undefined form as a result of fracturing.

When alumina is used as the microporous solid in the process according to the invention, the alumina may be contaminated with rare earth metal compounds, alkali metal compounds or alkaline earth metal compounds in the range from 0 to 20% by weight, more preferably from 0 to 10% by weight, based in each case on the solid mass used.

When the microporous solid used in the process according to the invention is a molecular sieve, this refers to molecular sieve having an average pore radius of from 0.1 to 20 Å, preferably from 1 to 10 Å.

When the 1,3-butadiene, before the actual hydrocyanation over the at least one nickel(0)-phosphorus catalyst, is contacted with the at least one microporous solid, it is advantageous subsequently to store and transport it, before the actual hydrocyanation of the 1,3-butadiene, at temperatures of less than 50° C., more preferably less than 20° C., in particular less than 0° C., in order to prevent polymerizations.

The inventive treatment of the feed streams for the above-described hydrocyanation with molecular sieve or alumina result in residual water contents in the reaction mixture of less than 1000 ppm, more preferably less than 100 ppm, in particular less than 10 ppm, of water.

The inventive treatment of the feed streams for the above-described hydrocyanation with alumina results in the achievement of residual contents in the reaction mixture of less than 500 ppm, more preferably less than 100 ppm, in particular less than 10 ppm, of tert-butylpyrocatechol (TBP).

EXAMPLE 1

On the Drying with Alumina

A stainless steel column having an internal diameter of 300 mm was charged with F200 alumina from Almatis (spheres having an average diameter of approx. 3 mm), in such a way that a 3000 mm-high bed was formed. The stainless steel column had a jacket which could be flowed through as desired with throttle-controlled 35 bar steam or brine from a brine cooling circuit. Thermoelements were introduced into the bed and could be used to monitor the temperature in the fixed bed. Both at the inlet of the column and downstream of the outlet from the column, a suitable measuring instrument for the determination of water in butadiene (from General Eastern, AMY 170) was used to measure the moisture content of the butadiene stream.

1,3-Butadiene was passed continuously through the bed at an internal temperature of 0° C. (brine cooling in the jacket space). Before entry into the column, this butadiene contained 367 ppm by weight of water. Downstream of the outlet from the column, the water content after flow through the bed for approx. 3 days was at a value of 0 ppm by weight.

EXAMPLE 2

On the Drying with Alumina

The degree to which the butadiene was free of water at the outlet of the drying tower which was described in Example 1 was tested with the following experiment: the cold butadiene from the drying tower was introduced via an immersed pipe into a vessel containing 10 l of pentenenitrile and tritolyl phosphite of the formula 1 dissolved therein (5% by weight based on pentenenitrile). The vessel was vented to a flare which combusted the offgas, and was continuously mixed by constant pumped circulation. Before and after the introduction of 100 l of liquid butadiene, the content of cresols in pentenenitrile was determined by GC analysis (GC: Hewlett Packard 5890, HP50-1 column, calibrated for m- and p-cresol, internal standard: benzonitrile). When 100 l of butadiene dried according to Example 1 was introduced (measurement with measuring instrument according to Example 1: 0 ppm by weight of water), the concentration of cresol changed from 0.07% by weight before the addition to 0.09% by weight.

Subsequently, undried butadiene was introduced directly into the vessel via a bypass around the drying tower. The butadiene had a measured water content of 371 ppm by weight. The cresol content in the pentenenitrile rose from 0.09% by weight to 1.65% by weight.

This example illustrates the need to dry butadiene before it is contacted with a catalyst system, suitable for the hydrocyanation, of Ni(0) complex with, for example, tritolyl phosphite as a ligand.

EXAMPLE 3

On the Regeneration of Laden Alumina

The apparatus described in Example 1 with the bed detailed there was charged with butadiene until the water content in the outlet stream had risen to a measured value of 50 ppm by weight of water. The butadiene feed was then stopped. Subsequently, the jacket was switched from brine cooling to heating with throttle-controlled 35 bar steam. The bed was then flowed through with 1 m$^3$/h of nitrogen and heated gradually to 210° C. over three days. When the end temperature had been attained, the steam heating was switched off and the bed was flowed through with nitrogen until 60° C. had been attained in the interior of the bed. Reconnecting the jacket again to brine cooling cooled the bed back to 0° C. and butadiene was then introduced again. After the wetting had been completed, the water meter at the outlet was brought back into operation. The measurements were again at 1 ppm by weight of water based on butadiene.

EXAMPLE 4

On the Drying with Molecular Sieve

A vessel made of boilerplate (diameter 50 mm) was charged with a 200 mm-high bed of molecular sieve from Karl Roth GmbH (product number 4062020) and cooled to 0°

C. using a jacket. Subsequently, butadiene was introduced at a mass flow rate of 100 g/h. At the outlet of the bed, a measuring instrument for determining water in butadiene (from General Eastern, AMY 170) did not find any detectable amounts of water over a period of two weeks. Accordingly, the butadiene was dry after it had flowed through the bed.

Continuous hydrocyanation of BD to 2M3BN/3PN

All experiments were carried out in a protective gas atmosphere.

Nickel(0) (m-/p-tolyl phosphite) corresponds to a solution of 0.9% by weight of nickel(0) with 19% by weight of 3PN and 79.1% by weight of m-/p-tolyl phosphite.

EXAMPLE 5

2.24 mol of butadiene dried over a bed of 4 Å molecular sieve, 1.62 mol of HCN and 14 mmol of Ni in the form of nickel(0)(m-/p-tolyl phosphite) were fed per hour into a stirred pressure reactor (pressure: 15 bar, internal temperature 105° C., residence time: approx. 40 min/reactor). According to quantitative analysis, the HCN conversion is quantitative (Vollhard titration). The 2M3BN/3PN ratio of the reaction effluent is determined by GC chromatography (GC area percent). The 2M3BN/3PN ratio was 1.82/1. The loss of Ni(0) based on product of value formed was 0.33 kg of Ni(0)/t of product of value (3PN/2M3BN).

EXAMPLE 6

2.05 mol of butadiene dried over a bed of alumina, 1.67 mol of HCN and 14 mmol of Ni in the form of nickel(0) (m-/p-tolyl phosphite) were fed per hour into a stirred pressure reactor (pressure: 15 bar, internal temperature 105° C., residence time: approx. 45 min/reactor). According to quantitative analysis, the HCN conversion is quantitative (Vollhard titration). The 2M3BN/3PN ratio of the reaction effluent is determined by GC chromatography (GC area percent). The 2M3BN/3PN ratio was 1.86/1. The loss of Ni(0) based on product of value formed was 0.23 kg of Ni(0)/t of product of value (3PN/2M3BN).

COMPARATIVE EXAMPLE A 2.09 mol of moist and stabilized butadiene (100 ppm of water, 100 ppm of TBC), 1.51 mol of HCN and 14 mmol of Ni in the form of nickel(0)(m-/p-tolyl phosphite) were fed per hour into a stirred pressure reactor (pressure: 15 bar, internal temperature 105° C., residence time: approx. 40 min/reactor). According to quantitative analysis, the HCN conversion is quantitative (Vollhard titration). The 2M3BN/3PN ratio of the reaction effluent is determined by GC chromatography (GC area percent). The 2M3BN/3PN ratio was 1.89/1. The loss of Ni(0) based on product of value formed was 0.48kg of Ni(0)/t of product of value (3PN/2M3BN).

What is claimed is:

1. A process for preparing 3-pentenenitrile by hydrocyanating 1,3-butadiene with hydrogen cyanide over at least one catalyst, the process comprising contacting 1,3-butadiene, hydrogen cyanide, or both the 1,3-butadiene and the hydrogen cyanide, with at least one microporous solid, and releasing the 1,3-butadiene, hydrogen cyanide, or both the 1,3-butadiene and the hydrogen cyanide, from the at least one microporous solid, hydrocyanating the 1-3-butadiene with hydrogen cyanide over at least one catalyst and regenerating the at least one microporous solid which had been contacted with 1,3-butadiene, hydrogen cyanide, or both the 1,3-butadiene and the hydrogen cyanide, by heating in an atmosphere comprising one or more gases selected from the group consisting of noble gases, air, and nitrogen, wherein the at least one catalyst comprises nickel (0).

2. The process according to claim 1, further comprising contacting hydrogen cyanide together with or separately from the 1,3-butadiene with the at least one microporous solid.

3. The process according to claim 1, wherein the at least one microporous solid includes tubes having beds, and the flow conditions of 1,3-butadiene are selected in such a way to provide plug flow characteristics over the at least one microporous solid.

4. A process for preparing 3-pentenenitrile by hydrocyanating 1,3-butadiene with hydrogen cyanide over at least one catalyst, in the presence of at least one microporous solid.

5. The process according to claim 4, further comprising regenerating the at least one microporous solid by heating in an atmosphere comprising one or more gases from the group consisting of noble gases, air, and nitrogen.

6. The process according to claim 1, wherein the 1,3-butadiene has a content of acetylene which is less than 1000 ppm.

7. The process according to claim 1, wherein the at least one microporous solid is selected from the group consisting of aluminas and molecular sieves and has a particle size of from 0.01 to 20 mm.

8. The process according to claim 1, wherein the microporous solid has a porosity which is between 0 and 80% based on the particle volume.

9. The process according to claim 1, wherein the microporous solid is in extrudate form or in round form as a result of fracturing.

10. The process according to claim 2, wherein the at least one microporous solid includes tubes having beds, and the flow conditions of the hydrogen cyanide are selected in such a way to provide plug flow characteristics.

11. The process according to claim 4, wherein the 1,3-butadiene has a content of acetylene which is less than 1000 ppm.

12. The process according to claim 4, wherein the at least one microporous solid is selected from the group consisting of aluminas and molecular sieves and has a particle size of from 0.01 to 20 mm.

13. A process for preparing 3-pentenenitrile by hydrocyanating 1,3-butadiene with hydrogen cyanide over at least one catalyst:

contacting at least one microporous solid with the 1,3-butadiene and hydrogen cyanide;

directing the, the 1,3-butadiene and the hydrogen cyanide that had contacted the at least one microporous solid to a hydrocyanation reaction system;

hydrocyanating the 1,3-butadiene with hydrogen cyanide over at least one catalyst and regenerating the at least one microporous solid that had been contacted with the 1,3-butadiene and hydrogen cyanide by heating in an atmosphere comprising one or more gases selected from the group consisting of noble gases, air, and nitrogen wherein the at least one catalyst comprises nickel (0).

14. The process according to claim 13, wherein the at least one microporous solid includes tubes having beds, and the flow conditions of 1,3-butadiene and hydrogen cyanide are selected to provide plug flow characteristics over the at least one microporous solid.

15. The process according to claim 13 wherein the 1,3-butadiene has a content of acetylene which is less than 1000 ppm.

16. The process according to claim 13 wherein the at least one microporous solid is selected from the group consisting of aluminas and molecular sieves and has a particle size of from 0.01 to 20 mm.

17. The process according to claim 16 wherein the microporous solid has a porosity which is between 0 and 80% based on the particle volume.

* * * * *